(12) United States Patent
Row et al.

(10) Patent No.: US 8,980,336 B2
(45) Date of Patent: Mar. 17, 2015

(54) METHOD FOR INHIBITING FREE RADICALS

(75) Inventors: Lie-Ching Row, Hsinchu (TW); Lien Tai Chen, Taoyuan (TW)

(73) Assignee: Industrial Technology Research Institute, Hsinchu (TW)

( * ) Notice: Subject to any disclaimer, the term of this patent is extended or adjusted under 35 U.S.C. 154(b) by 548 days.

(21) Appl. No.: 12/187,959

(22) Filed: Aug. 7, 2008

(65) Prior Publication Data

US 2008/0292689 A1    Nov. 27, 2008

Related U.S. Application Data

(63) Continuation-in-part of application No. 11/432,372, filed on May 12, 2006, now abandoned.

(30) Foreign Application Priority Data

Dec. 30, 2005  (TW) .............................. 94147657 A

(51) Int. Cl.
  *A61K 36/70*   (2006.01)
  *A61K 36/86*   (2006.01)
  *A61K 36/704*  (2006.01)

(52) U.S. Cl.
  CPC ............... *A61K 36/70* (2013.01); *A61K 36/704* (2013.01); *A61K 36/86* (2013.01)
  USPC ....................................................... 424/725

(58) Field of Classification Search
  None
  See application file for complete search history.

(56) References Cited

U.S. PATENT DOCUMENTS

| | | | |
|---|---|---|---|
| 5,411,733 A | 5/1995 | Hozumi et al. | |
| 5,723,136 A * | 3/1998 | Tanaka et al. | 424/401 |
| 5,837,257 A | 11/1998 | Tsai et al. | |
| 2006/0142382 A1 | 6/2006 | Morimoto et al. | |
| 2009/0263339 A1 | 10/2009 | Kyono et al. | |

FOREIGN PATENT DOCUMENTS

| | | |
|---|---|---|
| JP | 5-294819 A | 11/1993 |
| JP | 8-104646 A | 4/1996 |
| JP | 10-120546 A | 5/1998 |
| JP | 11-349435 A | 12/1999 |
| JP | 2000-319189 A | 11/2000 |
| JP | 2001-163757 A | 6/2001 |
| JP | 2003-212770 A | 7/2003 |
| JP | 2004-359732 A | 12/2004 |
| JP | 2005-60334 A | 3/2005 |
| JP | 2005-206466 A | 8/2005 |
| JP | 2005-281179 A | 10/2005 |
| JP | 2006-124355 A | 5/2006 |
| WO | WO 2006/126675 A1 | 11/2006 |

OTHER PUBLICATIONS

STN online, file CAPLUS, Acc. No. 2004:1078850, Doc. No. 142:147751 (Qu et al., Quangpuxue Yu Guangpu Fenxi (2004), vol. 24, No. 11, pp. 1407-1409), Abstract.*
Remington's Pharmaceutical Sciences (17th ed. 1985), pp. 1516, 1517.*
PUBMED online, file MEDLINE, PMID 10653484 (Sato et al., Free Radic. Res. (2000), vol. 32, No. 2, pp. 135-144), Abstract.*
JP 2002003336 A (2000), Abstract.*
Wen et al., "Apigenin's Extraction from the *Viola philippicassp munda* W.Becker and its Activity of Clearing Free Radical", Modern Food Science and Technology, vol. 22, No. 1, pp. 20-25, China Academic Journal Electronic Publishing House, 2006.
Kong et al., "Effects of Processing on Antioxidation of Radixet Rhizoma Rhei and Rhizoma Polygoni Cuspidati", China Journal of Chinese Materia Medica, vol. 26, No. 6, pp. 388-391, Jun. 2001.
Pan et al., "Separation and Activity of Antioxidant Components from *Polygonum Cuspidatum*", Fine Chemicals, vol. 22, No. 11, pp. 835-837 and 841, Nov. 2005.
Japanese Notice of Allowance, dated Dec. 6, 2011, for Japanese Application No. 2006-222466.

\* cited by examiner

*Primary Examiner* — Abigail Fisher
*Assistant Examiner* — Frank Choi
(74) *Attorney, Agent, or Firm* — Birch, Stewart, Kolasch & Birch, LLP

(57) ABSTRACT

A method for inhibiting free radical is provided. The method includes administering to a subject an effective amount of an herbal composition including *Polygonum cuspidatum* and/or *Viola yedoensis*. The herbal composition is suitable for mammalian subjects. The *Polygonum cuspidatum* is selected from fresh *Polygonum cuspidatum* herbage, and the *Viola yedoensis* is selected from fresh *Viola yedoensis* herbage.

2 Claims, No Drawings

METHOD FOR INHIBITING FREE RADICALS

CROSS REFERENCE TO RELATED APPLICATIONS

This application is a Continuation-In-Part of U.S. patent application Ser. No. 11/432,372, filed May 12, 2006 now abandoned and entitled "herb compositions inhibiting free radicals".

This Application claims priority of Taiwan Patent Application No. 94147657, filed on Dec. 30, 2005, the entirety of which is incorporated by reference herein.

BACKGROUND OF THE INVENTION

1. Field of the Invention

The invention relates to a method for inhibiting free radicals, and in particular relates to using an herbal composition comprising *Polygonum cuspidatum* and/or *Viola yedoensis* for inhibiting free radicals 2. Description of the Related Art Active free radicals may easily react with cells and DNA, resulting in aging and cancer.

Anti-oxidants such as vitamin E, vitamin C, carotenoids, trace elements, flavonoids, or phenol substances can effectively inhibit lipid peroxidation induced by free radicals. Anti-oxidants are cataloged into free radical terminators, reductants, chelating agents, oxygen scavengers, enzyme-type anti-oxidants, and peroxide decomposition agents. For human beings, anti-oxidants are important to resist disease.

Currently, various synthetic compounds capable of inhibition of free radicals have been developed. Most of them, however, result in environmental pollution. Thus, development of a natural anti-oxidant is important. Sources of natural anti-oxidants comprise vegetables, plants, herbal medicines, or fermentative foods.

BRIEF SUMMARY OF THE INVENTION

The invention provides a method for inhibiting free radical, comprising administering to a subject an effective amount of an herbal composition comprising *Polygonum cuspidatum* and/or *Viola yedoensis*.

The invention also provides an herbal composition capable of inhibition of free radicals comprising one of *Polygonum cuspidatum* and *Viola yedoensis* in an effective amount.

A detailed description is given in the following embodiments

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention provides a method for inhibiting free radical, comprising administering to a subject an effective amount of an herbal composition comprising *Polygonum cuspidatum* and/or *Viola yedoensis*.

The invention provides an herbal composition capable of inhibition of free radicals comprising one of *Polygonum cuspidatum* and *Viola yedoensis* in an effective amount. The *Polygonum cuspidatum* is present in an amount of about 0.01~10 wt % of the herb composition, preferably 0.01~1 wt %. The *Viola yedoensis* is present in an amount of about 0.01~10 wt % of the herb composition, preferably 0.01~1 wt %. The invention further provides an herbal composition capable of inhibition of free radicals comprising a mixture of *Polygonum cuspidatum* and *Viola yedoensis* in an effective amount, respectively. In the mixture, the *Polygonum cuspidatum* is present in an amount of about 0.01~10 wt % of the herb composition, preferably 0.01~1 wt %, and the *Viola yedoensis* is present in an amount of about 0.01~10 wt % of the herb composition, preferably 0.01~1 wt %. The herbal composition increases skin elasticity by about 1-5%. In addition the herbal composition increases water content of cuticle by about 20~40%.

The herbal composition is suitable for mammalian subjects, preferably human beings. The *Polygonum cuspidatum* is selected from fresh *Polygonum cuspidatum* herbage, and the *Viola yedoensis* is selected from fresh *Viola yedoensis* herbage.

The "subject" of the invention refers to any living individuals. The subjects include cells, tissues, organs, human or non-human mammals, e.g. a dog, a cat, a mouse, a rat, a cow, a sheep, a pig, a goat, or a primate, and expressly include laboratory mammals, livestock, and domestic mammals. In some embodiments, the mammals may be a human, or in others, the mammal may be a rodent, such as a mouse or a rat.

After extraction, the herbal composition can be dispersed in water, ethanol, or ethyl acetate, preferably water. Further, the liquid herbal composition may be freeze-dried to form powder.

Additionally, The herb composition of the invention can be formed into a cream, a gel, a lotion, a paste, an ointment, an emollient, a liposome, a nanosphere, a skin tonic, a mouth wash, an oral rinse, a shampoo, a mousse, a spray, a pack, a capsule, a tablet, a powder, a granule, a solution, a suspension, a patch, or an occlusive skin conditioning agent.

The herbal composition containing *Polygonum cuspidatum* has a free radical inhibition rate of about 90~100%. The herbal composition containing *Viola yedoensis* has a free radical inhibition rate of about 90~100%. The herbal composition containing a mixture of *Polygonum cuspidatum* and *Viola yedoensis* has a free radical inhibition rate of about 80~100%.

The herbal composition may be oral or external, but not limited thereto. The oral herbal composition may comprise health food product. The external herbal composition may comprise cosmetic products such as a treatment mask, a lotion, or a gel. In one embodiment, the herbal composition can be orally fed to the subject. In another embodiment, the herbal composition can be topically or externally applied to an affected area with a water-loss, elasticity, sebum secretion, a black spot, a pore number, or melanin in a subject.

Further, the herbal composition can be administered in combination with a second agent including, but not limiting to, an anti-oxidant agent, a vitamin, an antibiotic, a health food product, a cosmetic product or combinations thereof.

Example 1

600 g *Polygonum cuspidatum* herbage was thermal-extracted with 2 L ethanol at 60° C. for 4 hours and repeated 2~3 times. The extract solution was then re-concentrated to 200 ml. Next, 800 ml water and 300 ml n-hexene were added and extracted 3 times to form an aqueous layer and a n-hexene layer. The w-hexene layer was then re-concentrated (60° C., 2 hours) to form extracts thereof.

Next, the aqueous layer was extracted with 300 ml dichoromethane 3 times to form an aqueous layer and a dichoromethane layer. The dichoromethane layer was then re-concentrated (35° C., 2 hours) to form extracts thereof.

Next, the aqueous layer was extracted with 300 ml n-butanol 3 times to form an aqueous layer and a n-butanol layer. The w-butanol layer was then re-concentrated (70° C., 2 hours) to form extracts thereof. The last aqueous layer contained the *Polygonum cuspidatum* herbal composition. The *Polygonum cuspidatum* had concentration of 2000 μg/ml.

Finally, the aqueous layer was re-concentrated (80° C., 2 hours) and freeze-dried for 3 days to form powder. The herbal composition powder was stored at −20° C.

Free Radical Inhibition Rate Experiment 0.05 ml *Polygonum cuspidatum* extract solution and 0.05 ml ethanol were, respectively, added to 0.2 ml solution containing 10 mM ethylene diamine tetraacetic acid (EDTA), 1% gelatin, 0.2 mg/ml poly(alpha-methylstyrene) (PMS), 4 mg/ml nitroblue tetrazolium (NBT), 1 mM xanthine, and 0.1M phosphate buffer solution (pH7.8) at constant temperature of 25° C. Next, 0.05 ml xanthine oxidase solution and 0.05 ml phosphate buffer solution (0.1M, pH7.8) were, respectively, added to the *Polygonum cuspidatum*-containing solution and ethanol-containing solution. After mixing completely, the absorption at 540 nm of various solutions was measured by ELISA reader. The absorption is represented by A, B, C, and D. A represents the absorption of the solution containing *Polygonum cuspidatum* and xanthine oxidase. B represents the absorption of the solution containing *Polygonum cuspidatum* and phosphate buffer solution. C represents the absorption of the solution containing ethanol and xanthine oxidase. D represents the absorption of the solution containing ethanol and phosphate buffer solution.

The free radical inhibition rate of the *Polygonum cuspidatum* extract solution was obtained from the following formula.

$$\text{Free radical inhibition rate} = \frac{(C-D)-(A-B)}{(C-D)} \times 100\%$$

Example 2

600 g *Viola yedoensis* herbage was thermal-extracted with 2 L ethanol at 60° C. for 4 hours and repeated 2~3 times. The extract solution was then re-concentrated to 200 ml. Next, 800 ml water and 300 ml n-hexene were added and extracted 3 times to form an aqueous layer and a n-hexene layer. The n-hexene layer was then re-concentrated (60° C., 2 hours) to form extracts thereof.

Next, the aqueous layer was extracted with 300 ml dichoromethane 3 times to form an aqueous layer and a dichoromethane layer. The dichoromethane layer was then re-concentrated (35° C., 2 hours) to form extracts thereof.

Next, the aqueous layer was extracted with 300 ml w-butanol 3 times to form an aqueous layer and a n-butanol layer. The n-butanol layer was then re-concentrated (70° C., 2 hours) to form extracts thereof. The last aqueous layer contained the *Viola yedoensis* herbal composition. The *Viola yedoensis* had concentration of 2000 μg/ml.

Finally, the aqueous layer was re-concentrated (80° C., 2 hours) and freeze-dried for 3 days to form powder. The herbal composition powder was stored at −20° C.

Free Radical Inhibition Rate Experiment 0.05 ml *Viola yedoensis* extract solution and 0.05 ml ethanol were, respectively, added to 0.2 ml solution containing 10 mM ethylene diamine tetraacetic acid (EDTA), 1% gelatin, 0.2 mg/ml poly(alpha-methylstyrene) (PMS), 4 mg/ml nitroblue tetrazolium (NBT), 1 mM xanthine, and 0.1M phosphate buffer solution (pH7.8) at constant temperature of 25° C. Next, 0.05 ml xanthine oxidase solution and 0.05 ml phosphate buffer solution (0.1M, pH7.8) were, respectively, added to the *Viola yedoensis*-containing solution and ethanol-containing solution. After mixing completely, the absorption at 540 nm of various solutions was measured by ELISA reader. The absorption is represented by A, B, C, and D. A represents the absorption of the solution containing *Viola yedoensis* and xanthine oxidase, B represents the absorption of the solution containing *Viola yedoensis* and phosphate buffer solution. C represents the absorption of the solution containing ethanol and xanthine oxidase. D represents the absorption of the solution containing ethanol and phosphate buffer solution.

The free radical inhibition rate of the *Viola yedoensis* extract solution was obtained from the following formula.

$$\text{Free radical inhibition rate} = \frac{(C-D)-(A-B)}{(C-D)} \times 100\%$$

Example 3

600 g *Polygonum cuspidatum* herbage and 600 g *Viola yedoensis* herbage were thermal-extracted with 2 L ethanol at 60° C. for 4 hours and repeated 2-3 times. The extract solution was then re-concentrated to 200 ml. Next, 800 ml water and 300 ml n-hexene were added and extracted 3 times to form an aqueous layer and a s-hexene layer. The n-hexene layer was then re-concentrated (60° C., 2 hours) to form extracts thereof.

Next, the aqueous layer was extracted with 300 ml dichoromethane 3 times to form an aqueous layer and a dichoromethane layer. The dichoromethane layer was then re-concentrated (35° C., 2 hours) to form extracts thereof.

Next, the aqueous layer was extracted with 300 ml n-butanol 3 times to form an aqueous layer and a n-butanol layer. The n-butanol layer was then re-concentrated (70° C., 2 hours) to form extracts thereof. The last aqueous layer contained the *Polygonum cuspidatum* and *Viola yedoensis* herbal composition.

Finally, the aqueous layer was re-concentrated (80° C., 2 hours) and freeze-dried for 3 days to form powder. The herbal composition powder was stored at −20° C.

Free Radical Inhibition Rate Experiment 0.05 ml extract solution containing *Polygonum cuspidatum* and *Viola yedoensis* and 0.05 ml ethanol were, respectively, added to 0.2 ml solution containing 10 mM ethylene diamine tetraacetic acid (EDTA), 1% gelatin, 0.2 mg/ml poly(alpha-methylstyrene) (PMS), 4 mg/ml nitroblue tetrazolium (NBT), 1 mM xanthine, and 0.1M phosphate buffer solution (pH7.8) at constant temperature of 25° C. Next, 0.05 ml xanthine oxidase solution and 0.05 ml phosphate buffer solution (0.1M, pH7.8) were, respectively, added to the solution containing *Polygonum cuspidatum* and *Viola yedoensis* and the ethanol-containing solution. After mixing completely, the absorption at 540 nm of various solutions was measured by ELISA reader. The absorption is represented by A, B, C, and D. A represents the absorption of the solution containing *Polygonum cuspidatum*, *Viola yedoensis*, and xanthine oxidase. B represents the absorption of the solution containing *Polygonum cuspidatum*, *Viola yedoensis*, and phosphate buffer solution. C represents the absorption of the solution containing ethanol and xanthine oxidase, D represents the absorption of the solution containing ethanol and phosphate buffer solution.

The free radical inhibition rate of the extract solution containing *Polygonum cuspidatum* and *Viola yedoensis* was obtained from the following formula.

$$\text{Free radical inhibition rate} = \frac{(C-D)-(A-B)}{(C-D)} \times 100\%$$

Example 4

The example provides a health food product formed by the herbal composition. The content thereof comprises plant extracts (*Polygonum cuspidatum* and *Viola yedoensis*), cellulose (avicel 102), dicalcium phosphate, lactose, and corn starch.

Example 5

The example provides a lotion formed by the herbal composition. The content thereof comprises deionized water, xanthan gum, hydrogenated polyisobutene, isopropyl isostearate, glycerin, 1,3-butylene glycol, cestearyl alcohol, hyaluronic acid, steareth-21, steareth-2, dimethicone, plant extracts (*Polygonum cuspidatum* and *Viola yedoensis*), tocopheryl acetate, retinyl palmitate, 2-phenoxyethanol, imidazolidinyl urea, propylparaben, methylparaben, disodium EDTA, and fragrance.

Skin Analysis

30~50 health women applied the lotion to their left side faces and kept the other side clean. Skin was analyzed by various instruments every week until a 5$^{th}$ week. In this analysis, improvement of skin quality was estimated from water content of cuticle, water-loss rate, elasticity, sebum secretion, black spot, pore number, and melanin.

The analytical results are recited in Table 1. The results indicate that the lotion provided by the invention effectively reduced black spot, pore number, melanin, water-loss rate, and sebum secretion, and increase water content of cuticle and skin elasticity,

TABLE 1

| Black spot | Pore number | Melanin | Elasticity | Water content of cuticle | Water-loss rate | Sebum secretion |
|---|---|---|---|---|---|---|
| −15.0% | −12.6% | −22.3% | +3.0% | +30% | −8% | −2% |

While the invention has been described by way of example and in terms of the preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for inhibiting free radicals, comprising topically administering to a subject an effective amount of an herbal composition comprising at least one extract selected from the group consisting of a *Polygonum cuspidatum* extract, and a *Viola yedoensis* extract, wherein the *Polygonum cuspidatum* extract and the *Viola yedoensis* extract are prepared by a method comprising:

subjecting at least one of the *Polygonum cuspidatum* or *Viola yedoensis* to thermal-extraction with ethanol to form a crude extract;

extracting the crude extract with n-hexene and water to form a n-hexene layer and a aqueous layer;

extracting the aqueous layer with dichoromethane to form a dichoromethane layer and a second aqueous layer; and extracting the second aqueous layer with n-butanol to form a n-butanol layer and a third aqueous layer as the *Polygonum cuspidatum* extract, or the *Viola yedoensis* extract, and wherein, when present, the *Polygonum cuspidatum* extract is present in an amount of about 0.01-10 wt % of the herbal composition and, when present, the *Viola yedoensis* extract is present in an amount of about 0.01-10 wt % of the herbal composition, and wherein the herbal composition increases skin elasticity by about 1-5%.

2. A method for inhibiting free radicals, comprising topically administering to a subject an effective amount of an herbal composition comprising at least one extract selected from the group consisting of a *Polygonum cuspidatum* extract, and a *Viola yedoensis* extract, wherein the *Polygonum cuspidatum* extract and the *Viola yedoensis* extract are prepared by a method comprising:

subjecting at least one of the *Polygonum cuspidatum* or *Viola yedoensis* to thermal-extraction with ethanol to form a crude extract;

extracting the crude extract with n-hexene and water to form a n-hexene layer and a aqueous layer;

extracting the aqueous layer with dichoromethane to form a dichoromethane layer and a second aqueous layer; and extracting the second aqueous layer with n-butanol to form a n-butanol layer and a third aqueous layer as the *Polygonum cuspidatum* extract, or the *Viola yedoensis* extract, and wherein, when present, the *Polygonum cuspidatum* extract is present in an amount of about 0.01-10 wt % of the herbal composition and, when present, the *Viola yedoen-*

*sis* extract is present in an amount of about 0.01-10 wt % of the herbal composition, and
wherein the herbal composition increases water content of cuticle by about 20-40%.

* * * * *